(12) United States Patent
Ancona et al.

(10) Patent No.: US 8,986,615 B1
(45) Date of Patent: Mar. 24, 2015

(54) MOLECULAR CONCENTRATOR BASED ON THERMAL RATCHETING

(71) Applicants: Mario Ancona, Alexandria, VA (US); Arthur W. Snow, Alexandria, VA (US); F. Keith Perkins, Alexandria, VA (US)

(72) Inventors: Mario Ancona, Alexandria, VA (US); Arthur W. Snow, Alexandria, VA (US); F. Keith Perkins, Alexandria, VA (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 14/279,394

(22) Filed: May 16, 2014

(51) Int. Cl.
  *G01N 30/00* (2006.01)
  *G01N 1/40* (2006.01)
  *G01N 30/38* (2006.01)
  *B01D 53/04* (2006.01)

(52) U.S. Cl.
  CPC ............... *G01N 1/405* (2013.01); *G01N 30/38* (2013.01); *G01N 1/4022* (2013.01); *B01D 53/0462* (2013.01); *G01N 2030/008* (2013.01)
  USPC .......................................................... 422/88

(58) Field of Classification Search
  CPC .............. G01N 2030/008; G01N 2030/0085; G01N 2030/0075; G01N 2001/4022; G01N 1/405; B01D 53/0462
  USPC .............................. 73/23.41; 422/88; 436/178
  See application file for complete search history.

(56) References Cited

U.S. PATENT DOCUMENTS

| | | | | |
|---|---|---|---|---|
| 6,393,894 B1* | 5/2002 | Bonne et al. | | 73/23.2 |
| 6,792,794 B2* | 9/2004 | Bonne et al. | | 73/25.01 |
| 6,837,118 B2* | 1/2005 | Bonne et al. | | 73/863.12 |
| 7,578,167 B2* | 8/2009 | Bonne et al. | | 73/25.01 |
| 7,654,129 B2* | 2/2010 | Bonne et al. | | 73/23.21 |
| 7,779,671 B2* | 8/2010 | Bonne | | 73/25.01 |
| 2004/0060346 A1* | 4/2004 | Bonne et al. | | 73/61.44 |
| 2006/0228261 A1* | 10/2006 | Iwamoto et al. | | 422/88 |
| 2007/0028670 A1* | 2/2007 | Bonne et al. | | 73/31.05 |
| 2007/0274867 A1* | 11/2007 | Iwamoto et al. | | 422/88 |
| 2008/0163674 A1* | 7/2008 | Bonne et al. | | 73/31.05 |
| 2009/0100906 A1* | 4/2009 | Bonne | | 73/25.03 |
| 2010/0239436 A1* | 9/2010 | Bonne et al. | | 417/207 |
| 2011/0247394 A1* | 10/2011 | McBrady | | 73/23.41 |

OTHER PUBLICATIONS

P.E. Sheehan et al., "Detection Limits for Nanoscale Biosensors," Nano Letters, vol. 5, No. 4, pp. 803-807 (2005).
I. Voiculescu, et al., "Microfabricated chemical preconcentrators for gas-phase microanalytical detection systems," Trends in Analytical Chemistry, vol. 27, No. 4, pp. 327-343 (2008).

(Continued)

*Primary Examiner* — Peter Macchiarolo
*Assistant Examiner* — Nathaniel Kolb
(74) *Attorney, Agent, or Firm* — US Naval Research Laboratory; Joslyn Barritt

(57) ABSTRACT

A molecular concentrator comprising a thermal ratchet for driving molecules from one place to another. A plurality of conducting wires are arranged on or suspended above a substrate. Each of the wires is configured to strongly sorb a vapor of interest when the wire is at room temperature and to rapidly desorb the vapor when the wire is at an elevated temperature. By selectively heating and cooling the wires, vapor molecules incident on the wires can be directed in a desired manner, e.g., from the wires closest to the vapor-containing environment to a sensor.

20 Claims, 12 Drawing Sheets

(56) References Cited

OTHER PUBLICATIONS

W.A. Groves, et al., Analyzing organic vapors in exhaled breath using a surface acoustic wave sensor array with preconcentration: Selection and characterization of the preconcentrator adsorbent, Anal. Chim. Acta 371, 131-143 (1998).

I. Voiculescu, et al., "Micropreconcentrator for Enhanced Trace Detection of Explosives and Chemical Agents," IEEE Sensors J. 6, 1094-1104 (2006).

Q. Zhong et al., Characterization of a high-performance portable GC with a chemiresistor array detector, Analyst 134, 283-293 (2009).

M.D. Hsieh et al., "Limits of Recognition for Simple Vapor Mixtures Determined with a Microsensor Array," Anal. Chem. 76, 1885-1895 (2004).

B. Alfeeli et al., "MEMS-based multi-inlet/outlet preconcentrator coated by inkjet printing of polymer adsorbents," Sensors and Actuators B 133, 24-32 (2008).

R.E. Shaffer et al., "Multiway Analysis of Preconcentrator-Sampled Surface Acoustic Wave Chemical Sensor Array Data," Field Anal. Chem. Tech. 2, 179-192 (1998).

T. Nakamoto et al., "Odor-sensing system using preconcentrator with variable temperature," Sensors and Actuators B 69, 58-62 (2000).

C.E. Davis et al., "Enhanced detection of m-xylene using a preconcentrator with a chemiresistor sensor," Sensors and Actuators B 104, 207-216 (2005).

M.G. Ancona et al., "Scaling Properties of Gold Nanocluster Chemiresistor Sensors," IEEE Sensors Journal 6, 1403-1414 (2006).

M.G. Ancona, et al., "Analyte kinetics in a nanocluster-based chemiresistor: A case study," Sensors and Actuators B 177, 936-946 (2013).

* cited by examiner

MOLECULAR CONCENTRATOR BASED ON THERMAL RATCHETING

TECHNICAL FIELD

The present invention relates to the detection of vapors, and particularly to the collection of trace levels of vapor analyte for delivery to a point sensor.

BACKGROUND

Detection of analytes as dilute vapors requires not only a capable sensor, but also an efficient means for collecting, concentrating, and delivering the vapor analytes from the environment to the sensor. The need for the latter functionality and its challenges when the vapor is at trace levels are referred to as the "sampling problem".

In general, the difficulties of sampling, for both aqueous and vapor sensing, stem from diffusion limits, and specifically from the time required for the vapor molecules to "find" the sensor. See, e.g., P. E. Sheehan et al., "Detection Limits for Nanoscale Biosensors," *NANO LETTERS, Vol.* 5, No. 4, pp. 803-807 (2005).

These difficulties are relatively independent of sensor size. Although a larger sensor is more easily "found," it requires more molecules to generate the same response (though larger sensors do generally benefit from a lower noise floor).

A well-known approach for enhancing sensitivity/selectivity at the cost of response time is to use a pre-concentrator that consists of a large area/volume of adsorbent material that can gather vapor molecules over time, and then with rapid heating, pump the desorbed and now concentrated vapor over the sensor. See I. Voiculescu, et al., "Microfabricated chemical preconcentrators for gas-phase microanalytical detection systems," *Trends in Analytical Chemistry*, Vol. 27, No. 4, pp. 327-343 (2008). Of particular relevance to vapor sensing are W. A. Groves, et al., "Analyzing organic vapors in exhaled breath using a surface acoustic wave sensor array with pre-concentration: Selection and characterization of the preconcentrator adsorbent,*Anal. Chim. Acta* 371, 131-143 (1998); I. Voiculescu, et al., "Micropreconcentrator for Enhanced Trace Detection of Explosives and Chemical Agents," *IEEE Sensors J.* 6, 1094-1104 (2006); Q. Zhong et al., "Characterization of a high-performance portable GC with a chemiresistor array detector, *Analyst* 134, 283-293 (2009); M. D. Hsieh et al., "Limits of Recognition for Simple Vapor Mixtures Determined with a Microsensor Array," *Anal. Chem.* 76, 1885-1895 (2004); B. Alfeeli et al., "MEMS-based multi-inlet/outlet preconcentrator coated by inkjet printing of polymer adsorbents," *Sensors and Actuators B* 133, 24-32 (2008); R. E. Shaffer et al., "Multiway Analysis of Preconcentrator-Sampled Surface Acoustic Wave Chemical Sensor Array Data," *Field Anal. Chem. Tech.* 2, 179-192 (1998); T. Nakamoto et al., "Odor-sensing system using preconcentrator with variable temperature," *Sensors and Actuators B* 69, 58-62 (2000); and C. E. Davis et al., "Enhanced detection of m-xylene using a preconcentrator with a chemiresistor sensor," *Sensors and Actuators B* 104, 207-216 (2005).

Although useful, the pre-concentrator scheme remains diffusion-limited, both in the initial collection from the ambient, and in the transfer from the pumped air stream to the sensor. For example, although it might seem that much could be gained by having a large ratio between the areas of the pre-concentrator and sensor, the bigger this ratio the faster the air stream velocity over the sensor must be and the less time there will be available for analyte to out-diffuse onto the sensor, and a fundamental diffusion limit still remains.

The key to overcoming the diffusion limit and enabling efficient collection, concentration, and delivery of analyte molecules to a sensor thus appears to involve having a way of moving the molecules by means other than a carrier gas such as air. As already noted, no artificial method, material, or apparatus currently exists for doing this and thereby for surmounting the diffusion limitation.

However, there are biological sensing systems that do achieve extraordinary levels of sensitivity and it is thought that an essential aspect is a method for molecular delivery. For example, the antennae of moths serve as means of collecting exceedingly sparse pheromone molecules from the environment (as emitted by distant females) and then delivering them (without a carrier gas) to a receptor for detection. As discussed in the next section, the invention disclosed herein provides for the first time an artificial means for accomplishing similar molecular transport, though by a mechanism different from that used biologically.

SUMMARY

This summary is intended to introduce, in simplified form, a selection of concepts that are further described in the Detailed Description. This summary is not intended to identify key or essential features of the claimed subject matter, nor is it intended to be used as an aid in determining the scope of the claimed subject matter. Instead, it is merely presented as a brief overview of the subject matter described and claimed herein.

The present invention provides an apparatus and method for transporting desired analyte molecules in a vapor from an environment containing the vapor to a sensor. The present invention can simultaneously concentrate the selected vapor analyte and filter it from among interferents so that it can be more easily sensed and analyzed, and is therefore often referred to herein as a "molecular concentrator."

The basic mechanism or method of the molecular concentrator provided by the present invention can be described as a thermal ratchet for driving molecules from one place to another.

In accordance with the present invention, a plurality of heater wires are arranged on or suspended above a substrate. Each of the wires is configured to strongly sorb the vapor of interest at room temperature and to rapidly desorb it at an elevated temperature. By selectively heating one or more of the wires, a concentration of vapor molecules can be directed in a desired manner, e.g., from one wire to its neighbor or ultimately from the wires closest to the vapor-containing environment to a sensing device. In some embodiments, the surfaces of one or more of the wires may be bare metal, while in other embodiments they may have a coating that is configured to sorb one or more specified vapors of interest.

In an exemplary embodiment, the thermal ratchet in accordance with the present invention can serve as a molecular concentrator. In such an embodiment, the heater wires can be configured as an array of concentric wires with a sensor at the center. The thermal ratchet mechanism is then used to drive analyte molecules from the periphery (adjacent to the environment) to the sensor where they can be detected and analyzed.

DETAILED DESCRIPTION

The aspects and features of the present invention summarized above can be embodied in various forms. The following description shows, by way of illustration, combinations and configurations in which the aspects and features can be put into practice. It is understood that the described aspects, features, and/or embodiments are merely examples, and that one skilled in the art may utilize other aspects, features, and/or embodiments or make structural and functional modifications without departing from the scope of the present disclosure.

For example, although the present invention is described herein in the context of embodiments based on the use of an arrangement of heater wires, it may be possible to use other heater structures, materials, and/or geometries to accomplish the thermal ratcheting described herein. In addition, although the invention has been described as using coated heater structures, in some embodiments, appropriately configured uncoated structures made from materials that sorb and desorb vapor molecules as described may be also used. All such alternatives and other embodiments are deemed to be within the scope of the present invention.

The present invention provides an apparatus and method for transporting desired analyte molecules from an environment containing the vapor to a sensor. The present invention can simultaneously concentrate the selected vapor analyte and separate it from among interferents so that it can be more easily sensed and analyzed, and is therefore often referred to herein as a "molecular concentrator."

The basic mechanism or method of a molecular concentrator provided by the present invention can be described as a thermal ratchet for driving molecules from one place to another.

FIGS. 1A-1D are block diagrams illustrating the basic mechanism of a molecular concentrator based on thermal ratcheting in accordance with the present invention.

In the exemplary embodiment illustrated in FIGS. 1A-1D, a thermally ratcheting molecular concentrator in accordance with the present invention comprises a plurality of parallel wires 101*a-d* (or equivalent heater structures), shown in cross-section in the FIGURE, arranged on (or, as described below, suspended above) a substrate 105. Each of the wires is coupled to a source of heat energy, and in some embodiments, are also coupled to a source of cooling energy, where, as described below, the heat and/or cooling energy can be selectively applied to one or more of the wires. Each of the In the exemplary embodiment shown in FIGS. 1A-1D, each of the wires has a coating 102*a-d* on the surface thereof, wherein the coating is an absorbent material that selectively sorbs the vapor of interest at room temperature and rapidly desorbs the vapor at an elevated temperature. The coated wires 101/102*a-d* have a low thermal mass and can be heated by applying the heat energy into the wire, e.g., through resistive heating produced by running a current through the wire, and can be cooled by removing the heat energy or, some embodiments, by applying a cooling energy to the wire. When a wire is heated, the vapor of interest is desorbed from the surface of the wire, with the vapor then being resorbed on a neighboring wire which is at or below room temperature. In accordance with the present invention, by selectively applying and removing heat energy to the wires, it is possible to direct and focus vapor molecules incident on the wires a desired manner, e.g., from the wires closest to the vapor-containing environment to wires closest to a sensor.

Thus, at time t=0, as illustrated in FIG. 1A, vapor 100 is incident on a wire structure in which wire 101*a* is at room temperature while wires 101*b*, 101*c*, and 101*d* are at an elevated temperature. As illustrated in FIG. 1A, there is a strong sorption of the vapor (shown as vapor molecules 103) onto room-temperature wire 101*a* but not onto heated wires 101*b, c*, or *d*. Next, as depicted in FIG. 1B, at a time t=Δt, wire 101*a* is suddenly heated while wire 101*b* is rapidly cooled to room temperature (or below), with wires 101*c* and 101*d* remaining heated. The wires are thermally well isolated one from another, and so when wire 101*a* is cooled, (and with no other adsorbent surfaces nearby), most of the vapor molecules 103 that had been sorbed onto coating 101*b* on wire 101*a* will be rapidly desorbed from heated wire 101*a* and will be resorbed onto room-temperature wire 101*b*. In some cases, vapor molecules 103 may include one or more types of molecules 104 that are sufficiently less volatile at the temperatures/coatings used that they do not participate in the desorb/transfer process and, as illustrated in FIG. 1B, such molecules may remain on the heated wire 101*a*.

This process continues so that, at time t=2Δt shown in FIG. 1C, wire 101*b* is rapidly heated (with wires 101*a* and 101*d* also remaining heated) while wire 101*c* is rapidly cooled, which causes molecules 103 to be desorbed from coating 102*b* on wire 101*b* and be sorbed by coating 102*c* on wire 101*c*. Finally, and at time t=3Δt shown in FIG. 1D, wire 101*c* is rapidly heated (with wires 101*a* and 101*b* also remaining heated) while wire 101*d* is rapidly cooled to cause the molecules 103 to be desorbed from coating 102*c* on wire 102*a* and be sorbed by coating 102*d* on wire 101*d*. When the analyte vapor reaches a wire sufficiently close to an unheated sensor 106, that wire can be abruptly heated to cause the analyte vapor to desorb from the wire and thereby arrive at the sensor for detection.

Thus, in accordance with the present invention, by applying and removing heat from the wires in such a phased heating schedule, a controlled sorption/desorption process can be obtained which moves molecules from wire 101a to wire 101d in a desired manner without the need for a clean carrier gas or pumping of the vapor by a pressure head. In other words, this thermal ratcheting scheme produces the desired molecular drive with a greatly reduced diffusion overhead.

The thermal ratcheting method of this invention as just described can be utilized as an apparatus serving the practical purpose of collecting, concentrating, and transporting analyte molecules from the ambient to a sensor. In an exemplary embodiment, such an apparatus can be in the form of a concentric ring concentrator as illustrated in shown in FIG. 2, though other configurations may be possible within the scope of the present invention.

Figure 1:
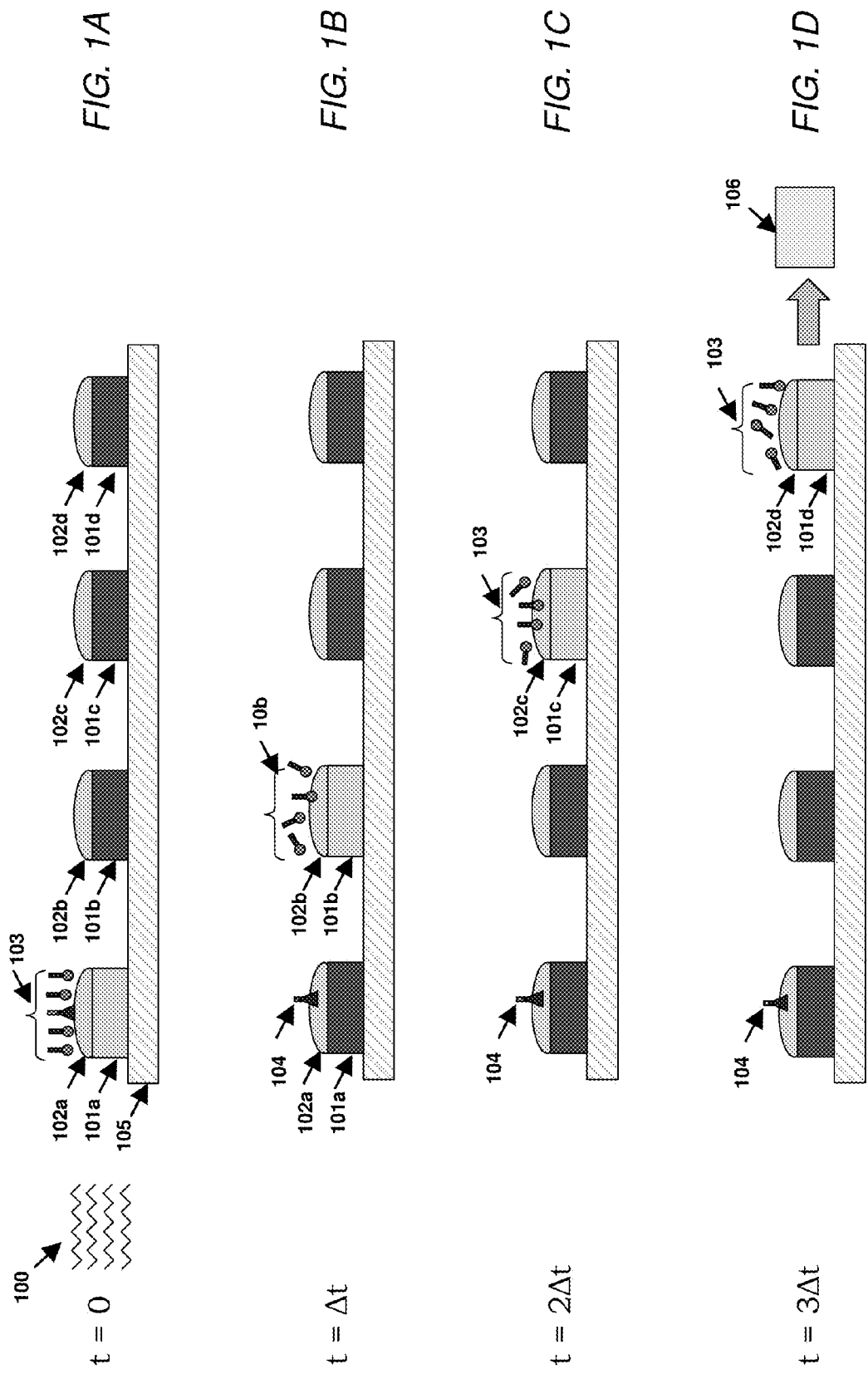
FIGS. 1A-1D are block diagrams illustrating the basic thermal ratcheting transfer mechanism by which the molecular concentrator of the present invention operates.
Figure 2:
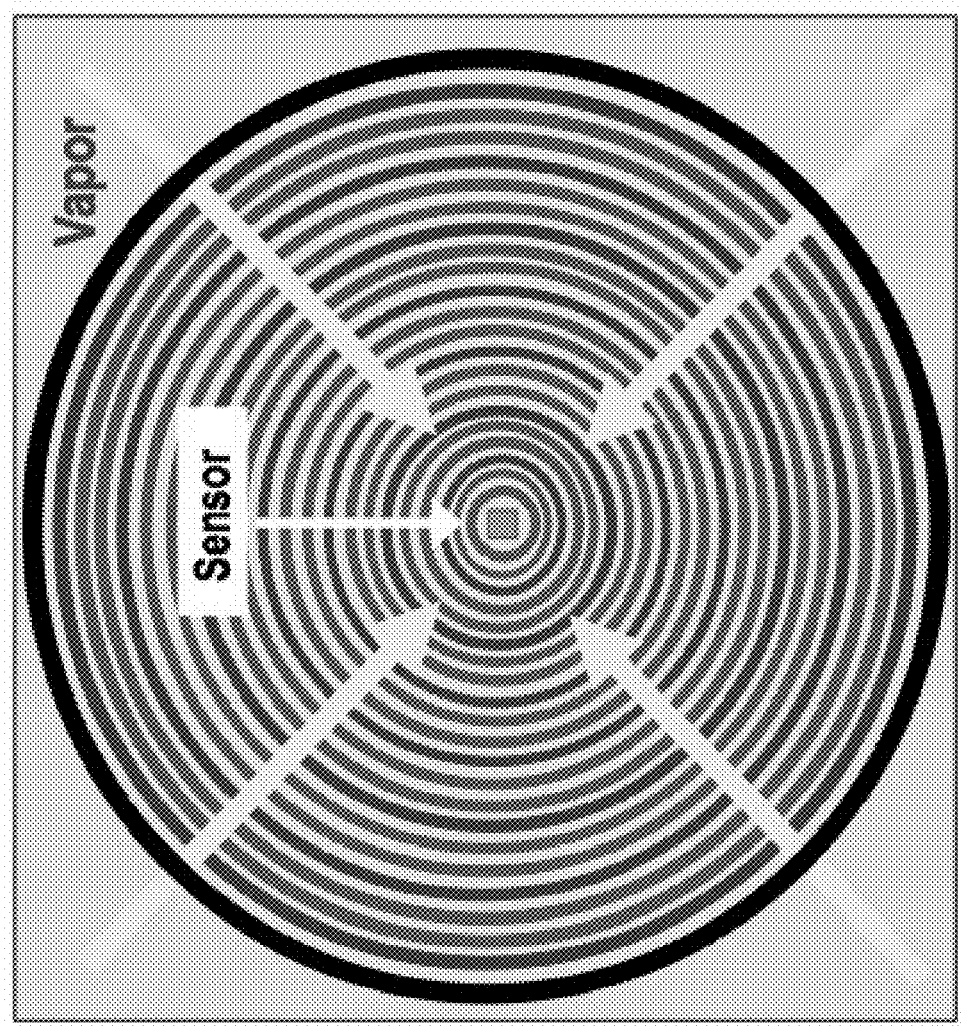
FIG. 2 is a block diagram illustrating aspects of an exemplary embodiment of a molecular concentrator based on thermal ratcheting in accordance with the present invention.

As illustrated in FIG. 2, such an apparatus can consist of a micro-fabricated two-dimensional circular configuration of concentric closely-spaced wire heating elements, with a sensor element located at the center of the circular arrangement of wires. In some embodiments, the wires can be situated directly on a substrate, while in others they can be suspended above the substrate to improve the thermal isolation of each wire from the others. The surfaces of the wires may be bare metal or may be treated to alter the surface roughness and/or chemical composition for the purpose of enhancing the quantity and/or selectivity of the vapor sorption. The surfaces of the wires may also be coated with a thin film designed to sorb vapors into its matrix for the purpose of further enhancing the quantity and/or selectivity. The thickness of such coatings may range from a molecular monolayer (~0.5 nm) to a thin film (~0.1 mm). The apparatus' overall dimension may range from the $mm^2$ to $cm^2$ scale, with the width and spacing between the electronic wire heating features ranging from under a micron to a millimeter or more.

Each of the individual wires in the wire pattern is connected to a current source configured to selectively apply current to individual wires to cause the wire to become heated through resistive heating when the current through the wire is turned on, and then to return to room temperature when the current through the wire is turned off. Thus, in accordance with the present invention, by the application of appropriately phased heat pulses such as the phased heating depicted in FIGS. 1A-1D, molecules in a vapor incident on the wire structure are driven from the periphery of the structure to the sensor located at the center. The converging nature of the design leads to a geometrical concentration of any molecules in the ambient that are sorbed at the periphery and are capable of following the sorption/desorption cycles at the selected temperatures and frequencies for the sorption-desorption characteristics of a particular coating.

In addition, by appropriately configuring one or more of the arrangement of the wires, the coating thereon on the wires, and the temperatures or times applied, the composition of the molecules moved from wire to wire can be selectively tuned, e.g., to enhance the concentration of molecules of interest and/or to suppress the concentration of interferent molecules in the vapor reaching the sensor.

In embodiments where a surface treatment or a coating is applied to the heater wire surface, the treatment/coating can be designed to have an affinity for a targeted vapor of interest and/or to provide enhancement of quantity and selectivity of sorbed vapors by way of reversible chemical interactions. Such surface treatments or coating depositions position a density of molecular sites onto the wire surface or within the thin film matrix of the coating that have an affinity to interact with vapors of interest and to serve as sites for vapor adsorption on the treated surface or for vapor absorption within the matrix of the film. Both the density and binding strength of such vapor sorption sites exceed those of the bare metal heater wire surface. A degree of selectivity for targeted vapors may also be included in the design of a surface treatment or a coating for vapor sorption. The types of reversible chemical interactions include acid-base, charge-transfer, dipole-dipole, and van der Waals. Physical and chemical processes for surface treatments include energy beams (laser, electron, ion beams), plasmas (various gas phase chemicals), and chemical depositions (organometallic chemical vapor depositions, atomic layer depositions, self-assembled monolayers). Thin film coatings include a variety of organic polymers (many classes of thermoplastics, elastomers, and thermosets), inorganic polymers (several classes), non-volatile small molecules and salts, and these coatings may be deposited by solution aerosol deposition, mechanical transfer, or vapor deposition polymerizations. The key requirements are that the surface treatment or coating film have compatible processing with the concentrating apparatus of this invention, have a thermal stability over the temperature range of operation, and have a reversible interaction (sorption and desorption) with vapors of interest over the temperature range of operation.

The structures illustrated in FIGS. 1A-1D and FIG. 2 capture the basic principles of the thermal ratchet method and apparatus for analyte collection and delivery. However, an actual implementation must also contend with certain limitations imposed by kinetic theory, thermodynamics, and chemistry. One such limit is the conflict between a desire to get the wires close together for efficient transfer and the need to keep them thermally isolated so that their temperatures can be manipulated independently. One approach would be to make substrate 105 be a material like $SiO_2$ that has a very low thermal conductivity. A better isolation approach is to suspend the wires as air bridges, e.g., supported by widely separated posts defined on the substrate, in which case the dominant inter-wire coupling is from the weak thermal conduction through the air.

Figure 3:
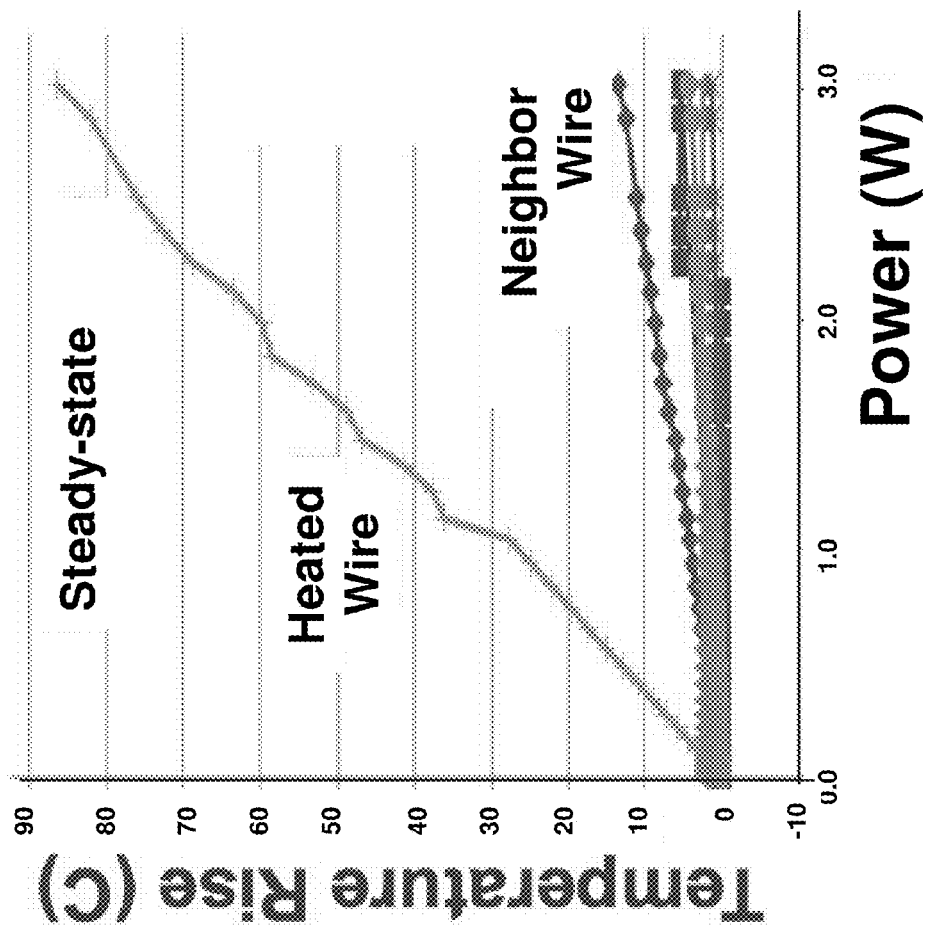
FIG. 3 is a plot illustrating aspects of suspended wire heating utilized in a molecular concentrator based on thermal ratcheting in accordance with the present invention.

A plot illustrating an experimental demonstration of the thermal isolation possible with this strategy is presented in FIG. 3 where the steady-state temperatures of a heated wire and of its neighbors (with the nearest parallel neighbor being about 1 μm distant) is plotted as a function of the applied power.

A critical issue regarding the thermal-ratchet idea relates not to its performance but to proving its operation. This is a challenging task given the trace amounts of analyte and the micron-scale geometries, and therefore to demonstrate the thermal-ratchet method as well as to understand some of its design issues a variety of numerical simulations and experiments were performed.

That the system of heated wires is on a scale that is large (~60 nm) compared to the mean free path in air (so that the Knudson number is less than 0.1) means the analyte desorption and flow can be modeled using the compressible Navier-Stokes equations with the analyte transport treated using a convection-diffusion equation and the boundary conditions describing the heater wire temperatures and the desorption. In an exemplary flow regime, viscous effects tend to dominate with the Reynolds' number Re of roughly 0.1 and the importance of thermal effects is measured by an estimated Prandtl number Pr of about 0.7.

The equations governing the motion of the molecules along the wires are then the conservation of air mass (where c is the local air density and u is its local velocity)

$$\frac{\partial c}{\partial t} + c\nabla \cdot u = 0;$$

the conservation of momentum in the air (where m is the average atomic mass of the air molecules, p is the air pressure and μ is the air viscosity)

$$mc\frac{\partial u}{\partial t} + \nabla \cdot \left(pI - \mu\nabla u + \frac{2}{3}\mu I \nabla \cdot u\right) = 0;$$

the convection equation for the analyte molecules in the air (with density a and diffusion constant $D_a$)

$$\frac{\partial a}{\partial t} + \nabla \cdot (D_a \nabla a - ua) = 0;$$

and the heat conduction equation (where T is the local temperature, $C_v$ is the specific heat of the air, and κ is its thermal conductivity)

$$mcC_v\frac{\partial T}{\partial t} + \kappa \nabla^2 T = 0.$$

The absorption/desorption kinetics of the molecules as they interact with the heated/cooled wires in accordance with the present invention can be expressed as $$\frac{\partial s}{\partial t} = k_S(r_S a - s) = -n \cdot J_a,$$

where s is the adsorbed analyte density, $k_s$ and $r_s$ are reaction rate constants, $J_a$ is the flux of adsorbing analyte, and n is the surface normal vector, and with the Maxwell-Smoluchowski slip condition being expressed as $$u = \frac{2-\sigma_v}{\sigma_v} \frac{u\partial u/\partial y}{\rho\sqrt{2RT/\pi}} + \frac{3}{4}\frac{Pr(\gamma-1)\kappa}{\gamma\rho RT}\frac{\partial T}{\partial x},$$

where u is the slip velocity at the surface, and γ is the ratio of specific heats.

Figure 4:
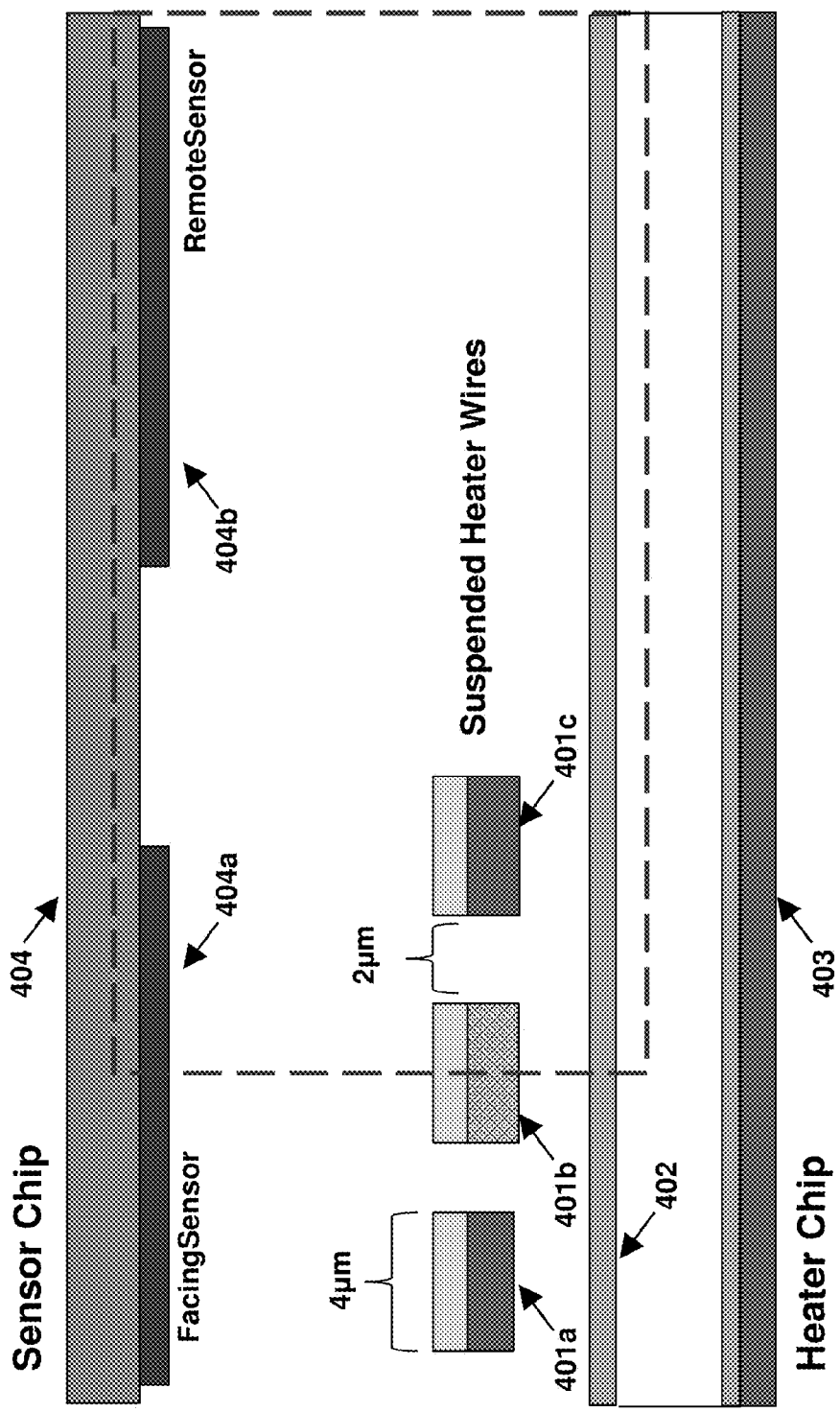
FIG. 4 is a block diagram illustrating aspects of an exemplary embodiment of a molecular concentrator based on thermal ratcheting in accordance with the present invention.

To examine the basic behavior of molecules in a thermal ratcheting molecular concentrator in accordance with the present invention, the inventors simulated a molecular concentrator having the exemplary structure illustrated in FIG. 4.

As shown in FIG. 4 such an exemplary structure consisted of three long adsorbent material-coated heater wires 401a/401b/401c (shown in cross-section in FIG. 4). To prevent the heating of one wire by neighboring wires, the wires are modeled as being suspended over a substrate 402 and separated from one another by a distance of 2 μm as shown in the FIGURE. As described above with respect to FIG. 1A-1D, in accordance with the present invention, wires 401a/b/c are resistively heated by means of an electric current passing therethrough, e.g., from heater chip 403 shown in FIG. 4, and then are brought back to room temperature to cause vapor molecules to be sorbed/desorbed and thus moved along from one wire to another. Opposite and parallel to heater chip 403 is a sensor chip 404 chip containing sensors that in the experiments serve to monitor the thermal-ratchet operation. These sensors include a facing sensor 404a, which is situated directly above and facing the suspended wires, and a remote sensor 404b, which is situated at some distance away from the suspended wires.

Figure 5:
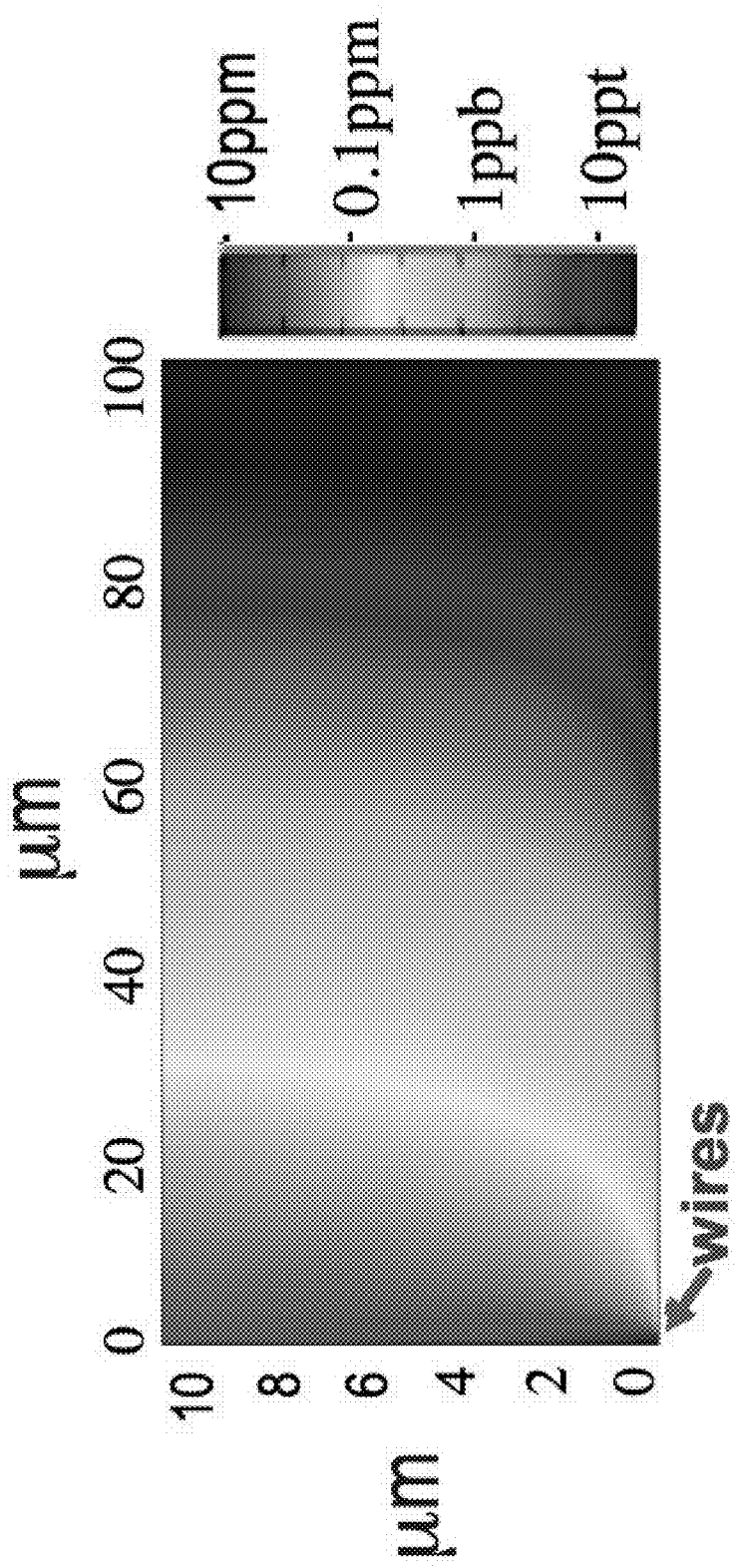
FIG. 5 is a plot showing a simulated heating profile of a single wire having an initial sub-monolayer coating of adsorbed analyte in accordance with the present invention.

A snapshot from a simulation of this structure is shown in the contour plot in FIG. 5, which displays the concentration of an analyte of interest in a plume of analyte vapor emitted following abrupt heating of an analyte-loaded wire. As is clear from the plot, the greatest concentration of analyte reaches the sensors (which reside on the top surface of the plot, and with the facing sensor at the left edge) is where they approach most closely to the heated wire. From numerous calculations of this type the thermal-ratchet action can be captured in the computer and its characteristics studied including the expected response signals that would be measured by the sensors.

The summary plots shown in FIGS. 6A-6D show the efficiency of transfer of molecules at each step from a suddenly heated wire onto a cold neighboring wire under specified conditions and assuming no sidewall adsorption.

Figure 6B:
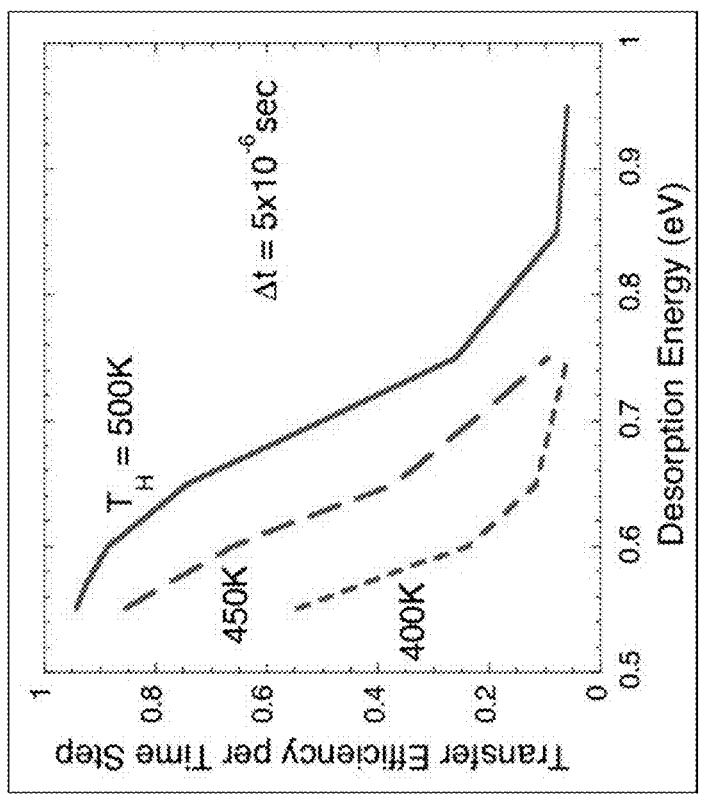
FIGS. 6A-6D are plots showing simulated aspects of analyte transfer and concentration in accordance with the present invention.
Figure 6A:
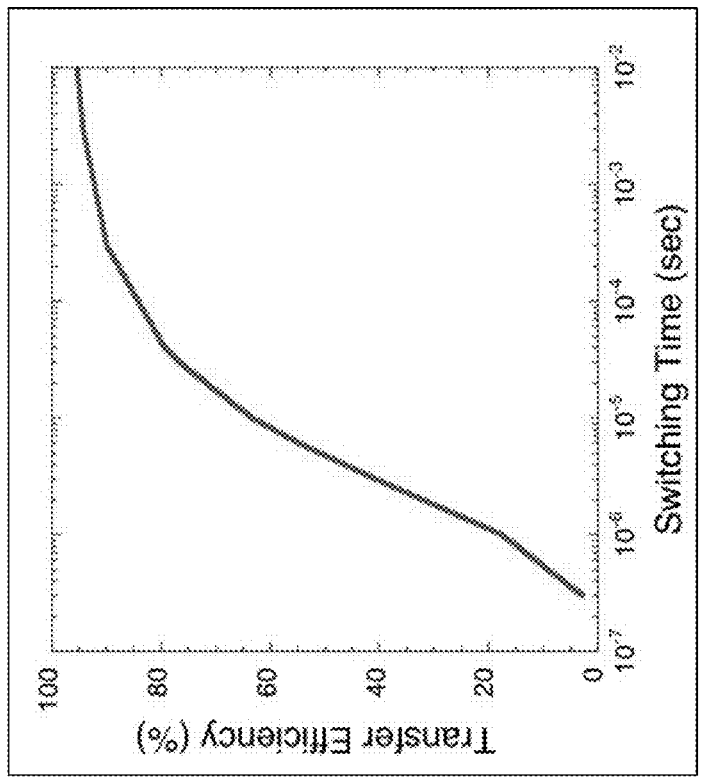

The effect of the time allotted for the transfer is studied in FIG. 6A, and, unsurprisingly, it is found that the transfer efficiency is lower if a shorter time is available for the molecules to move and is greater when a longer time is available, and if sufficient time is available, the transfer efficiency can be quite high (e.g., >90%).

Figure 6D:
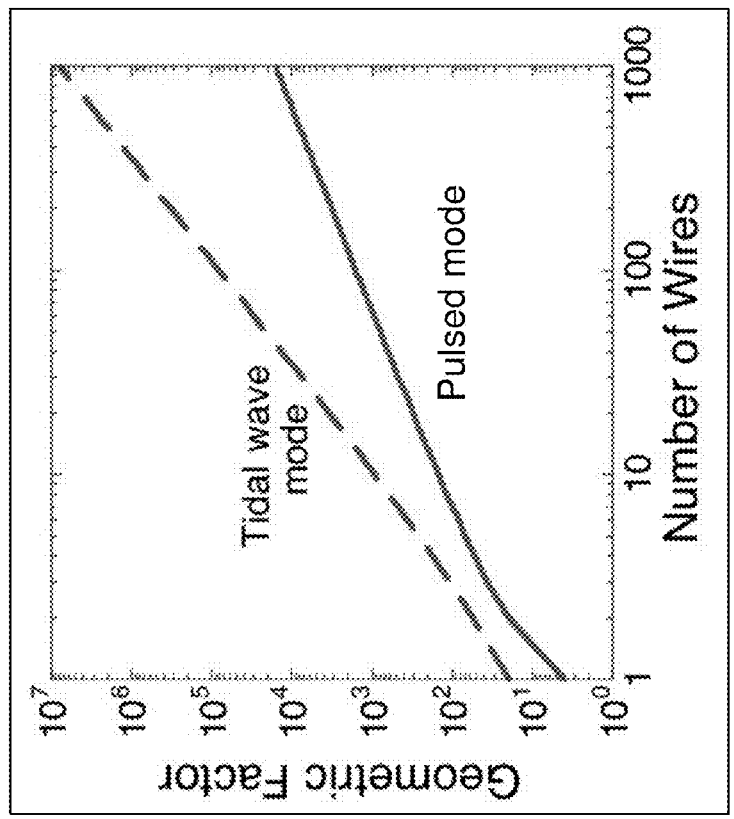
Figure 6C:
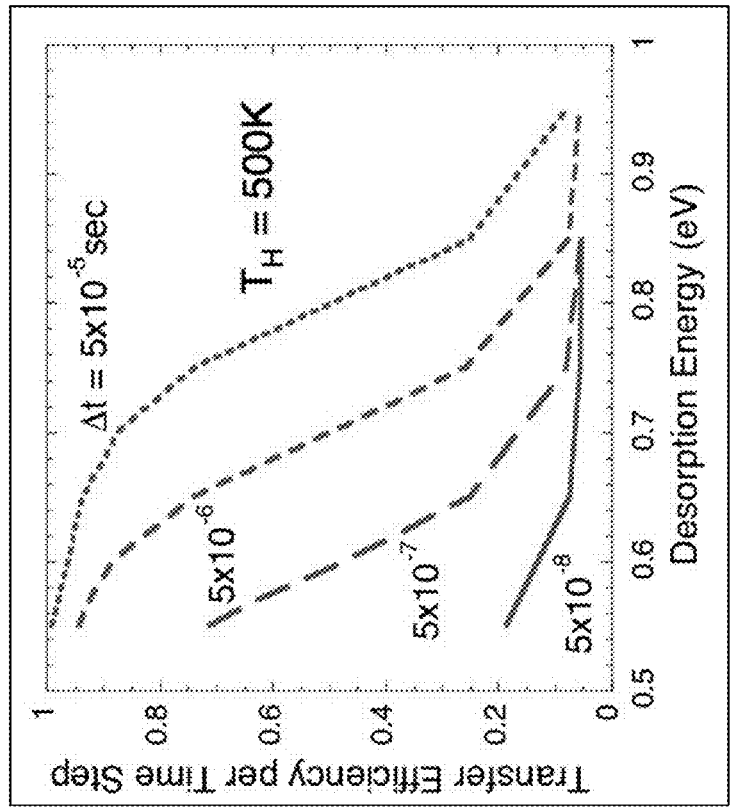

The idea that the thermal-ratchet can be used to obtain selectivity by distinguishing molecules according to their volatility and coating sorptive affinity was investigated next, and the inventors found that such selectivity can be obtained either by controlling the temperature to which the wires are heated, as shown in FIG. 6B or by controlling the switch time, as shown in FIG. 6C. In each case, the transfer efficiency is seen to depend on desorption energy, and so by proper choice of the temperature and switch time, one could separate analytes that have differing desorption energies. In this process, the constituent with the lower desorption energy would be driven forward by the thermal ratchet, while the constituent with the higher desorption energy would remain adsorbed to the heater wires.

A final summary plot in FIG. 6D shows the ability to concentrate the analyte vapor that the concentric ring concentrator shown in FIG. 2 would be expected to exhibit. The two curves shown in FIG. 6D correspond to two different modes of sequencing the heat pulses applied to the heater wires. The "pulsed" mode is identical to that depicted in FIGS. 1A-1D in which the wires are heated and cooled in sequence. In contrast, in the "tidal wave" mode, once wires are heated they are left heated so that a step in wire heating propagates inward through the concentrator, pushing analyte on to the unheated wires before it and toward the sensor at the center. As can be seen from the plots, irrespective of the number of wires used, the "tidal wave" mode of heating the wires is more efficient than the "pulsed" mode, though in both cases substantial levels of molecular focusing are seen to be possible.

To further demonstrate the invention, the inventors performed experiments investigating the basic thermal ratchet mechanism by which the analyte transfer depicted in FIGS. 1A-1D is effected. For this purpose, a combined heater-sensor configuration such as that illustrated in FIG. 4 was used, with a second sensor chip placed parallel to the chip with the heater wires at a variable distance. This chip allowed the molecular action to be monitored using two sensors, one a "facing" sensor that was situated immediately across from the heated wires and the other a "remote" sensor positioned a few millimeters away. For these experiments, triethylamine (TEA) vapor was used as a test analyte, the adsorbent material on the heater wires was a carboxylic acid (COOH)-functionalized amine-epoxy polymer coating, and the sensors were MIME chemiresistors based on a thin film of gold nanoclusters having a passivating surface ligand composed of mercaptohexanoic acid. For a discussion of the COOH-amine chemistry in a sensor context, see M. G. Ancona, A. W. Snow, F. K. Perkins, B. Pate, and D. Park, "Analyte kinetics in a nanocluster-based chemiresistor: A case study," *Sensors and Actuators B* 177, 936-946 (2013). Among other things, this paper showed that the MIME sensor made with gold nanoclusters coated with mercaptohexanoic acid is extraordinarily selective for amines like TEA, and highly sensitive with a minimum detectable level below 1 part per billion (1 ppb).

Figure 7:
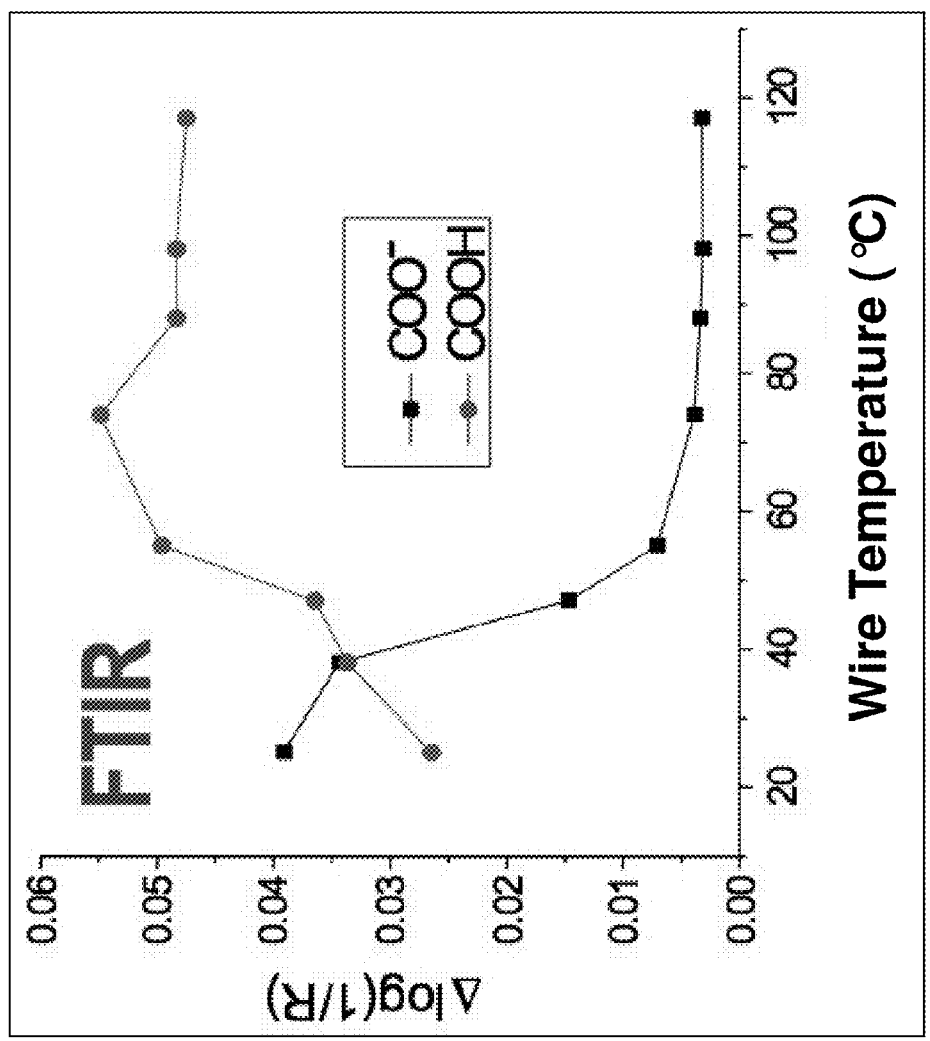
FIG. 7 is a plot showing the results of a Fourier transform infrared spectroscopy (FTIR) analysis of an exemplary COOH-functionalized epoxy film exposed to a triethylamine (TEA) analyte in accordance with one or more aspects of the present invention.

FIG. 7 examines the TEA absorption characteristics of the COOH-functionalized epoxy polymer film used as the coating/absorbent covering the heater wires in the specific test implementation of the present invention under discussion. The traces shown in the FIGURE represent the temperature variations in carboxylic acid (COOH) and carboxylate (COO—) groups in the film following exposure to TEA as measured by Fourier transform infrared (FTIR) spectroscopy. As can be seen from FIG. 7, as the film is heated above a temperature of about 40° C., there is a disappearance of COO— groups and an appearance of COOH groups in the film. This shows that the COOH-functionalized epoxy coating has the desired property of being both a good sorber of the analyte TEA at room temperature and a good desorber of the TEA when raised in temperature by an amount readily accessible through resistive heating.

To develop an expectation of what might be seen in the experiments performed on the heater-sensor test structure under discussion, two additional simulations were performed by solving the compressible Navier-Stokes equations given earlier. Both simulations are based on an initial state in which a 0.1 monolayer of TEA was adsorbed onto a center heater wire.

Figure 8B:
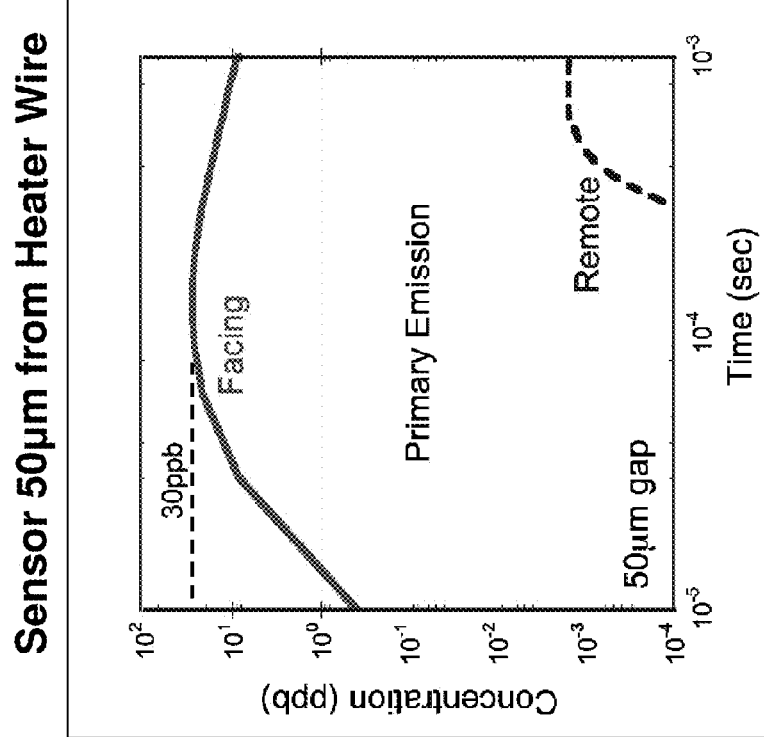
FIGS. 8A and 8B are plots showing a simulated response of the facing and remote sensors due to a pulse of analyte emitted from a heater wire covered with a layer of TEA and then abruptly heated (primary emission).
Figure 8A:
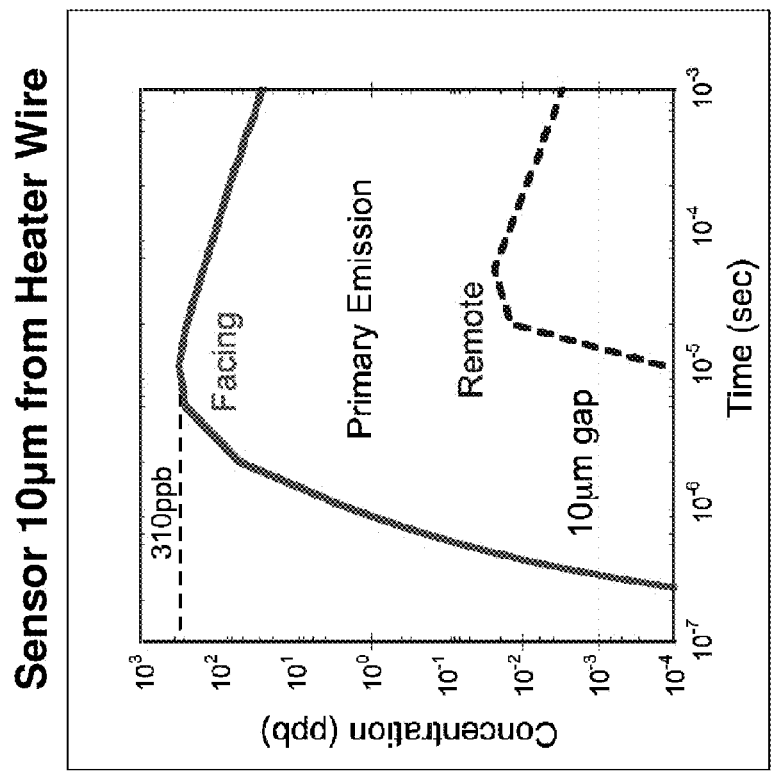

In the first simulation, the center wire was heated to form a "primary emission" consisting of the burst of the desorbed analyte from the heated wire. The simulated sensor responses to this primary emission for the "facing" and "remote" sensors on the sensor chip were collected as a function of time as shown in FIGS. 8A and 8B, where FIG. 8A plots the measured analyte concentration for a sensor chip situated 10 μm away from the heater chip and FIG. 8B plots the concentration for a sensor chip situated 50 μm away. All of the plotted concentrations are well within the known detection range of the MIME sensors for TEA (<1 ppb as noted earlier). Evident in the plots is the expected result that the concentration measured at the "remote" sensor peaks both more slowly and to a smaller magnitude than that seen on the facing sensor, and this is true irrespective of the distance between the sensor chip and the heater chip. As also would be expected, the narrower (10 μm versus 50 μm) gap between the sensor and heater chips provides a higher measured analyte concentration because the ambient volume into which the initial analyte concentration from the wire is diluted is smaller.

The second set of simulations models the crucial proof-of-principle experiment of the present invention that looks to demonstrate the thermal ratchet mechanism by examining the elementary step of molecules being transferred from one wire to another. The simulation again begins with analyte adsorbed on the center wire. The center wire is then rapidly heated, and, as described above, the analyte is desorbed form the heated wire to form a primary emission of analyte. In addition, as studied in the simulation that produced the "transfer efficiency" plot shown in FIG. 6A and as described above with respect to FIGS. 1A-1D, in accordance with the present invention, some of the desorbed analyte will be re-adsorbed on neighboring cold wires, i.e., will effect the desired transfer of molecules from one wire to another. To demonstrate that this transfer has indeed occurred, one of the neighboring wires is rapidly heated and any transferred analyte is desorbed from that wire forming a "secondary emission" that can be measured by the sensors.

Figure 9B:
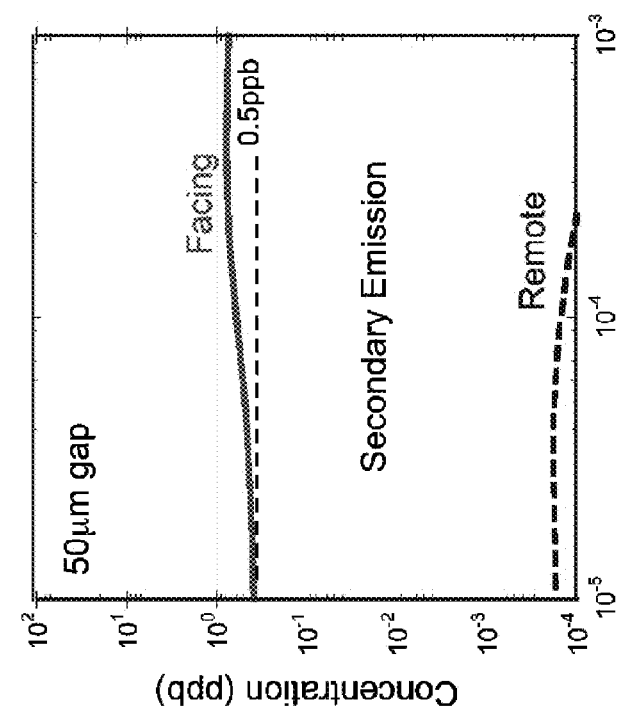
FIGS. 9A and 9B are plots showing a simulated response of the facing and remote sensors due to a pulse of analyte emitted by an abruptly heated second heater wire to which TEA analyte had previously been transferred from a first heater wire (secondary emission).
Figure 9A:
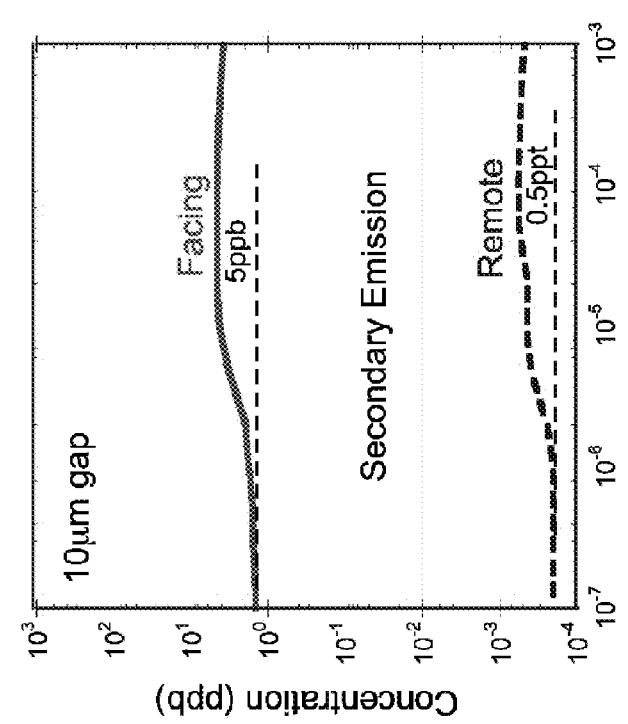

The simulated sensor responses associated with such a secondary emission are shown in FIGS. 9A and 9B for heater-sensor gaps of 10 μm and 50 μm, respectively. As seen in these figures, in both cases, only the facing sensor detects an appreciable level of analyte, with the measured response consisting of not only the secondary emission plume associated with the heating of the second wire but also a background associated with the primary emission previously desorbed from the first wire. As can be seen from the plots in FIGS. 9A and 9B, the levels of detected analyte associated with the secondary emission are quite small—0.5 ppb for a facing sensor 10 μm from the heater chip and 0.5 ppb for a facing sensor 50 μm away—but should still be large enough to be detected by a high-performance sensor such as the MIME sensor described above.

Figure 10B:
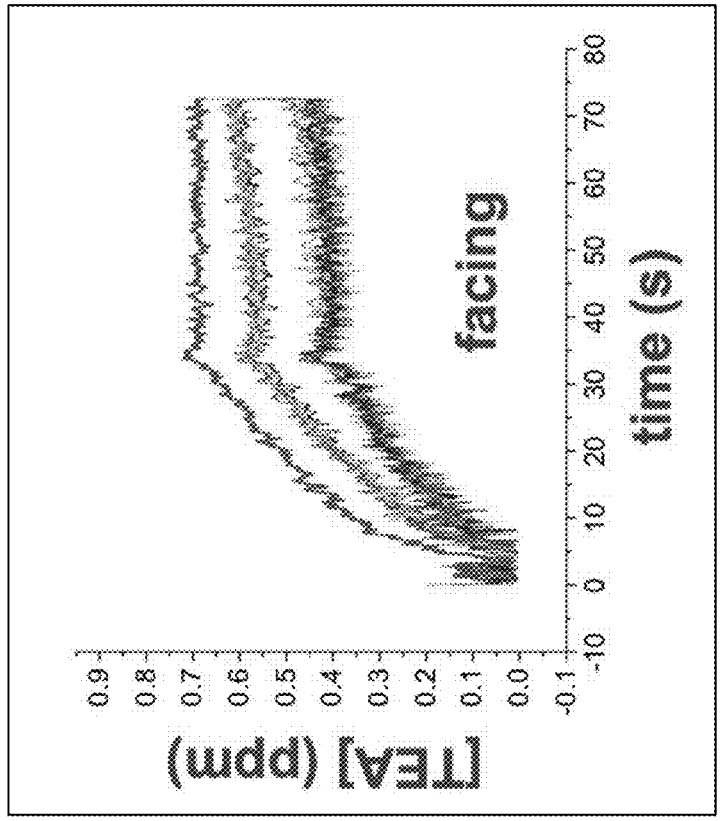
FIGS. 10A and 10B are plots showing measured sensor characteristics for the facing sensor in response to (primary) emission of TEA from a heated wire in accordance with the present invention
Figure 10A:
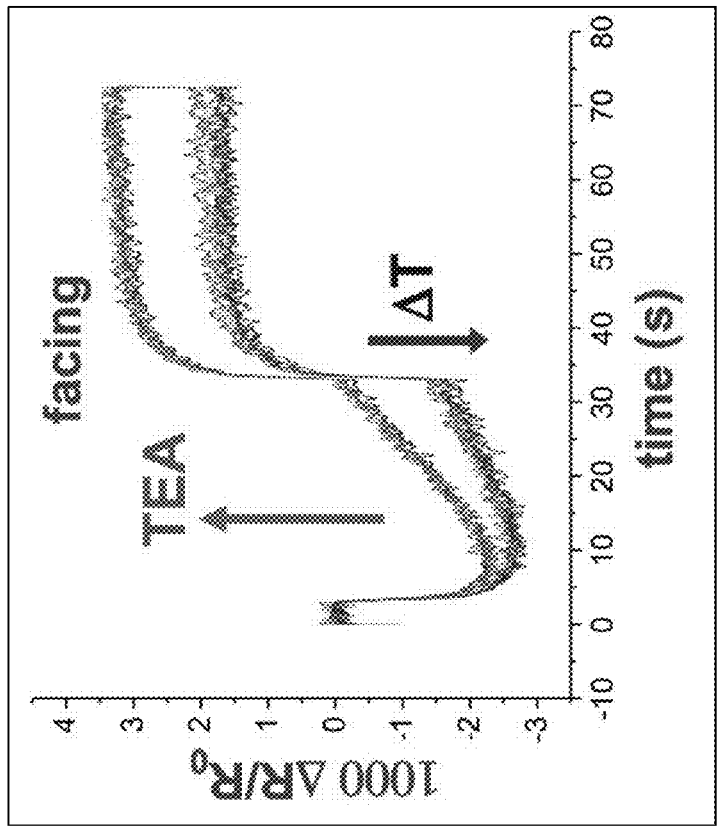

FIGS. 10A and 10B show measured sensor responses for the facing sensor in an experiment looking at the primary emission of TEA from a suddenly heated wire as studied previously in simulation in FIGS. 8A and 8B. For the experiment, a single wire was loaded with TEA simply by heating all of the wires except the center one during exposure to the vapor analyte. A heat pulse applied to this wire produced the primary emission that was then monitored using the sensor. This measurement was made more complicated by the fact that the heater wire pulse raises the temperature of the nearby sensor slightly (by about 0.15 C, and primarily due to heat conduction through the air) and that in itself produces a sensor response (see FIG. 10A). However, the thermal response and the response to the TEA are opposite in sign, with the former relatively abrupt and fixed in magnitude, and so the two signals can readily be distinguished. The TEA response alone (with the thermal response subtracted off) is plotted in FIG. 10B, and the measured magnitudes and temporal behavior are found to be quite similar to the simulated behavior plotted in FIGS. 8A and 8B.

In both FIGS. 10A and 10B the multiple traces are associated with sequential heat pulses, with the TEA signal observed to drop with each successive pulse as the TEA on the wire becomes increasingly depleted. Thus, the MIME sensors in the heater-sensor test structure are experimentally demonstrated to be capable of detecting the TEA analyte emitted from a single heated wire.

Figure 11:
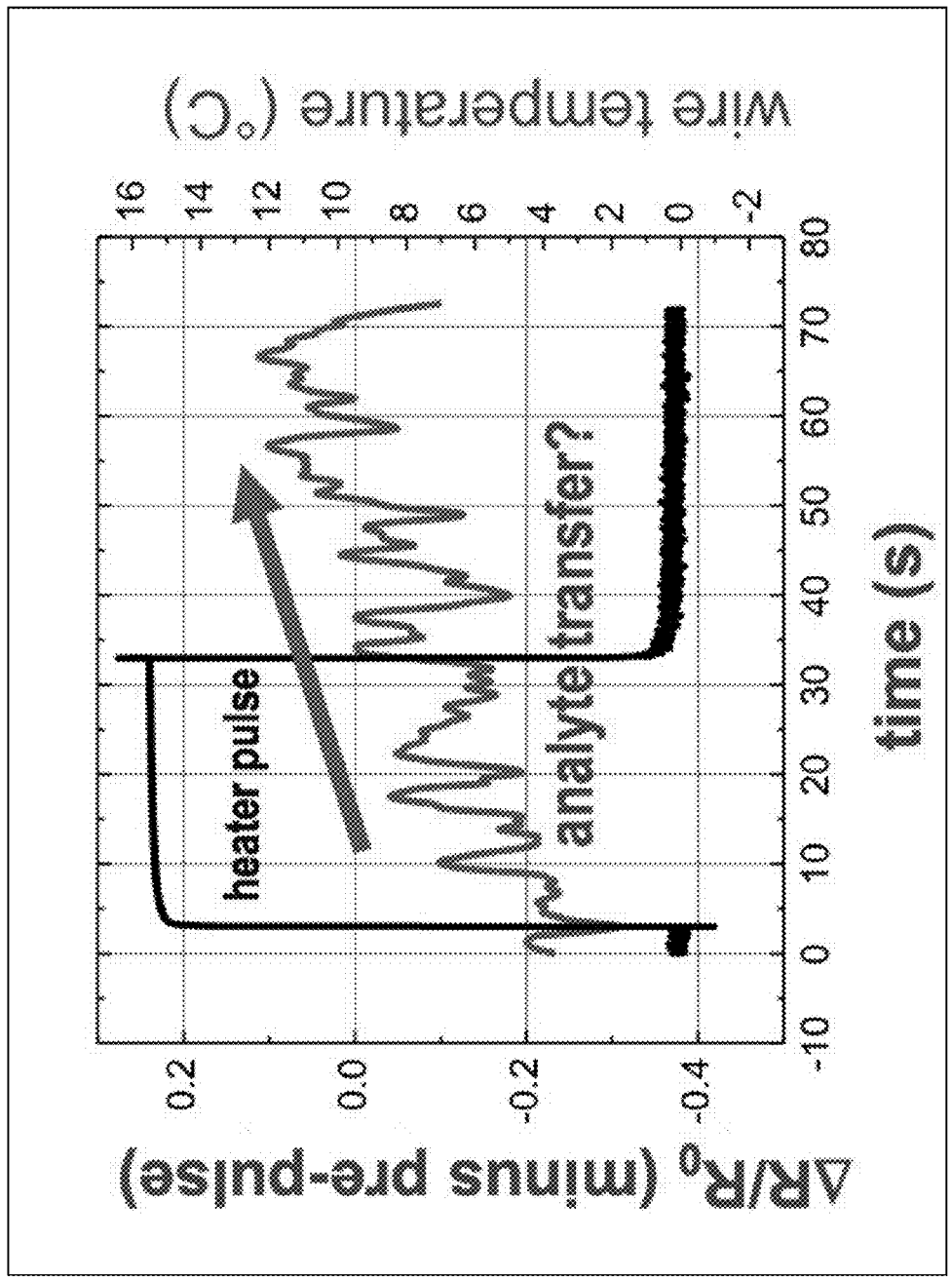
FIG. 11 is a plot showing measured sensor characteristics for the facing sensor from in response to (secondary) emission of TEA in accordance with the present invention.

The plot in FIG. 11 shows the results of the proof-of-principle experiment studied previously in simulation in FIG. 9 in which one looks for the "secondary emission" from a suddenly heated wire of the TEA that had previously been transferred to it from a neighboring wire using the thermal-ratchet mechanism. FIG. 11 displays the heater wire pulse (the black line and the right-hand axis giving the temperature) lasting from time=3 sec to time=32 sec, and the facing sensor response to the TEA with the thermal background subtracted off as in FIG. 10B. Although not entirely unambiguous, a response does appear to be seen both during and following the heater pulse, and in accord with the simulations in FIG. 9 is quite small (though still above the detection limit of the sensor). That a secondary emission response seems to be observed is experimental evidence in support of the proof-of-principle notion that analyte transfer between wires has been observed and that the underlying thermal-ratchet mechanism is indeed capable of driving molecules.

In summary, the present invention provides a unique method based on a thermal ratcheting mechanism for moving molecules on a substrate with a much reduced diffusion loss and provides an apparatus for exploiting this mechanism to concentrate, separate, and transport chemical vapor analytes to a sensor component. In an exemplary embodiment, the apparatus is in the form of a concentric ring concentrator that herds molecules into a very small region for purposes of transduction and detection, but one skilled in the art will readily recognize that other configurations may be possible.

Advantages and New Features

The advantages and new features of the method and apparatus of the present invention over existing approaches may be summarized as follows:

The present invention overcomes the diffusion limits that inflate the concentrations and times required for conventional point sensing systems to perform at the sub-part-per-billion concentration levels of interest (e.g., for vapor sensing of explosives).

The present invention enables nanosensors (with potential advantages for few-molecule sensitivity, selectivity, power consumption, etc.) to be used at low concentrations without prohibitively long collection times.

The present invention provides a new method (based on time and temperature) for selectivity enhancement in point sensing.

The present invention eliminates the need for a sampling carrier gas or its supporting components (storage reservoir or air purification scrubber, pumping system and associated power requirement).

The present invention eliminates the need for a conventional pre-concentrator and/or micro-gas chromatograph.

The present invention can provide rapid operation even at low analyte concentrations.

An apparatus in accordance with the present invention can be fabricated using simple planar lithographic fabrication.

The present invention is adaptable to a wireless distributed network system.

An apparatus in accordance with the present invention can be implemented in a miniature size adaptable for garment and small vehicle attachments, and for handheld and autonomous applications.

An apparatus in accordance with the present invention has lower power requirements than other miniaturized detection systems.

Although particular embodiments, aspects, and features have been described and illustrated, it should be noted that the invention described herein is not limited to only those embodiments, aspects, and features, and it should be readily appreciated that modifications may be made by persons skilled in the art.

The present application contemplates any and all modifications within the spirit and scope of the underlying invention described and claimed herein, and all such embodiments are within the scope and spirit of the present disclosure.

What is claimed is:

1. An apparatus for directing vapor molecules to a desired location, comprising:

an arrangement of heater structures coupled to a selectively controllable source of heat energy configured to selectively apply heat energy to the heater structures, each of the heater structures having a low thermal mass and being configured to rapidly heat upon an application of the heat energy and to rapidly cool in the absence of the heat energy, the heater structures further being thermally isolated one from another so that a heating or a cooling of one structure does not heat or cool a neighboring structure;

wherein each of the heater structures is configured to sorb molecules from a vapor incident on the structures when the structure is cool and to desorb at least some of the sorbed molecules when the structure is heated, at least some of the desorbed molecules then being sorbed by a neighboring structure;

wherein the heat energy is selectively applied and removed from one or more of the heater structures to cause the molecules from the vapor to selectively sorb and desorb from one heater structure to another at the desired location in a desired manner; and wherein the arrangement of heater structures comprises a plurality of thermally isolated metal wires in a concentric arrangement, each of the wires being coupled to the source of heat energy such that the heat energy can be selectively applied and removed from each individual wire;

wherein the heat energy is selectively applied and removed from one or more of the metal wires to cause the molecules from the vapor to move from wires located at a periphery of the concentric arrangement to wires located at the center of the concentric arrangement.

2. The apparatus according to claim 1, wherein the arrangement of heater structures comprises a plurality of thermally isolated metal wires, each of the wires being coupled to the source of the heat energy such that the heat energy can be selectively applied and removed from each individual wire.

3. The apparatus according to claim 1, wherein the heater structures cool to room temperature in the absence of the heat-generating force.

4. The apparatus according to claim 1, further comprising a source of cooling energy coupled to the heater structures; wherein the heater structures are heated upon application of the heat energy and are cooled to below room temperature upon an application of the cooling energy.

5. The apparatus according to claim 1 wherein the heater structures have a surface treatment comprising an alteration in the surface composition of the heater structures, the surface treatment being configured to adsorb molecules from the vapor when the structure is cool and to desorb some of the adsorbed molecules when the structure is heated.

6. The apparatus according to claim 1, wherein the heater structures have a coating thereon, the coating comprising an absorptive material configured to absorb molecules from the vapor when the structure is cool and to desorb at least some of the sorbed molecules when the structure is heated.

7. The apparatus according to claim 6, wherein the coating is configured to selectively desorb specified analyte molecules so that a vapor that reaches the desired location has an enhanced concentration of the specified analyte molecules.

8. The apparatus according to claim 6, wherein the coating is configured to selectively retain specified analyte molecules when the heat-conducting material is cooled so that a vapor that reaches the desired location has a reduced concentration of the specified analyte molecules.

9. The apparatus according to claim 6, wherein at least one of the coating and the heat energy is configured to selectively produce a desired concentration of a desired analyte molecule in the vapor that reaches the desired location.

10. The apparatus according to claim 6, wherein the coating is configured to have an affinity and temperature behavior appropriate for the selective direction of amine vapors to the desired location.

11. The apparatus according to claim 1, wherein the desired location is a specified heater structure proximate to a sensor configured to receive and analyze at least one analyte molecule in the vapor;
wherein when the specified heater structure is cooled, analyte molecules adsorbed on the specified heater structure are desorbed from the specified heater structure and are received by the sensor.

12. An apparatus for sensing molecules in a vapor, comprising:
an arrangement of heater structures coupled to a selectively controllable heater chip configured to selectively apply heat energy to the heater structures, each of the heater structures having a low thermal mass and being configured to rapidly heat upon an application of the heat energy and to rapidly cool in the absence of the heat energy, the heater structures further being thermally isolated one from another so that a heating or a cooling of one structure does not heat or cool a neighboring structure; and
a sensor chip comprising at least one sensor configured to receive and analyze at least one molecule from the vapor;
wherein each of the heater structures is configured to sorb molecules from a vapor incident on the structures when the structure is cool and to desorb at least some of the sorbed molecules when the structure is heated, at least some of the desorbed molecules then being sorbed by a neighboring structure;
wherein the heat energy is selectively applied and removed from one or more of the heater structures to cause the molecules from the vapor to selectively sorb and desorb from one heater structure to another in a desired manner;
wherein when the molecules from the vapor reach a specified heater structure, heat energy is removed from the specified heater structure to cause the specified heater structure to cool;
wherein the heater structures comprise a plurality of thermally isolated metal wires in a concentric arrangement with the sensor located at the center of the concentric arrangement, each of the metal wires being coupled to the heater chip such that the heat energy can be selectively applied and removed from each individual wire;
wherein the wires are selectively heated and cooled to cause analyte molecules from the vapor to move from wires located at a periphery of the concentric arrangement to the sensor; and
wherein analyte molecules desorb from the cooled heater structure and are adsorbed by the sensor.

13. The apparatus according to claim 12, wherein the arrangement of heater structures comprises a plurality of thermally isolated metal wires, each of the metal wires being coupled to the heater chip such that the heat energy can be selectively applied and removed from each individual wire.

14. The apparatus according to claim 12, wherein the heater chip comprises a current source, the heater structures being configured to be heated through resistive heating when current from the current source is applied thereto.

15. The apparatus according to claim 12, wherein the heater structures have a surface treatment comprising an alteration in the surface composition of the heater structures, the surface treatment being configured to adsorb molecules from the vapor when the structure is cool, and to desorb some of the adsorbed molecules when the structure is heated.

16. The apparatus according to claim 12, wherein at least one of the heater structures is coated with an absorptive material coating configured to absorb molecules from the vapor when the structure is cool and to desorb at least some of the sorbed molecules when the structure is heated.

17. The apparatus according to claim 16, wherein the coating is configured to selectively desorb specified molecules to selectively produce a desired concentration of a desired analyte molecule in the vapor that reaches the sensor.

18. The apparatus according to claim 16, wherein at least one of the coating and the heat energy is configured to selectively produce a desired concentration of a desired analyte molecule in the vapor that reaches the sensor.

19. The apparatus according to claim 16, wherein the coating is configured to have an affinity and temperature behavior appropriate for the selective direction of amine vapors to the sensor.

20. A method for directing an analyte molecule in a vapor to a desired location, comprising:
selectively applying and removing a heat energy to one of a plurality of heater structures having a low thermal mass and being configured to rapidly heat upon an application of the heat energy and to rapidly cool in the absence of the heat energy, the heater structures further being thermally isolated one from another so that a heating or a cooling of one structure does not heat or cool a neighboring structure;
wherein each of the heater structures is configured to sorb molecules from a vapor incident on the structures when the structure is cool and to desorb at least some of the sorbed molecules when the structure is heated, at least some of the desorbed molecules then being sorbed by a neighboring structure; and
wherein the heat energy is selectively applied and removed from one or more of the heater structures to cause the molecules from the vapor to selectively sorb and desorb from one heater structure to another at the desired location in a desired manner.

* * * * *